United States Patent [19]

Morscher et al.

[11] Patent Number: 4,936,859
[45] Date of Patent: Jun. 26, 1990

[54] REINFORCEMENT FOR ANCHORING A PROSTHESIS STEM

[75] Inventors: Erwin W. Morscher, Basel; Otto Frey, Winterthur, both of Switzerland

[73] Assignees: Sulzer Brothers Limited, Winterthur; Protek AG, Berne, both of Switzerland

[21] Appl. No.: 290,436

[22] Filed: Dec. 27, 1988

[30] Foreign Application Priority Data

Jan. 14, 1988 [CH] Switzerland ............................. 0130/88

[51] Int. Cl.⁵ ............................. A61F 2/30; A61F 2/28; A61F 2/36
[52] U.S. Cl. ............................. 623/18; 623/16; 623/23
[58] Field of Search ............... 623/16, 16 A, 18, 22, 623/23, 20

[56] References Cited

U.S. PATENT DOCUMENTS 4,064,567  12/1977  Burstein et al. ............... 623/18
4,276,659   7/1981  Hardinge ...................... 623/16 A
4,745,914   5/1988  Frey et al. ................... 623/16 X

FOREIGN PATENT DOCUMENTS 0220427  5/1988  European Pat. Off. .
2842847  4/1980  Fed. Rep. of Germany .
 251248  7/1983  France .
2052267  1/1981  United Kingdom .

Primary Examiner—Ronald L. Frinks
Attorney, Agent, or Firm—Kenyon & Kenyon

[57] ABSTRACT

The reinforcement is formed of a peg from which a plurality of flaps extend with slots formed between adjacent flaps. The flaps serve to separate a bone cement bed within the interior of the reinforcement from a layer of a compacted spongy tissue externally of the reinforcement. The slots between the flaps extend over the entire height of the reinforcement and permit substantial spreading or widening of the flaps radially in order to adapt to the individual operation cavity and to anchoring stems of different cross-sectional sizes and shapes.

5 Claims, 1 Drawing Sheet

REINFORCEMENT FOR ANCHORING A PROSTHESIS STEM

This invention relates to a reinforcement for anchoring a prosthesis stem. More particularly, this invention relates to a mesh reinforcement for anchoring an endoprosthesis stem.

Heretofore, the various types of reinforcements have been known for anchoring a stem of an endoprosthesis within a medullated bone with the use of bone cement. For example, German PS No. 2 842 847 describes a reinforcement which is filled internally with bone cement and back-filled externally with compacted spongy tissue when implanted in a medullated bone. This reinforcement is comprised of a peripherally closed conically narrowing shell having a mesh-like wall. However, such a construction is relatively difficult to adapt to individual radial and peripheral conditions of an operation bone cavity since cross-sectional widening of the shell cross-section are possible only to the extent permitted by the expandability of the mesh-like wall.

Accordingly, it is an object of the invention to provide a reinforcement which can be adapted to individual circumstances in all directions of a bone cavity.

It is another object of the invention to provide a reinforcement which can be adapted to the shape of a bone cavity for implanting of a stem of a prosthesis.

Briefly, the invention provides a reinforcement for anchoring an endoprosthesis stem which is comprised of a peg for mounting in an operatively prepared bone cavity and a plurality of elongated flaps secured to and extending from the peg. These flaps are made of a porous construction, for example being made of mesh material or of a lattice construction. In addition, the flaps are spaced apart to define slots therebetween over the entire length of the flaps.

The flaps may be secured to the peg at the distal ends, such as by welding.

When being placed in a prepared bone cavity, the flaps may be deformed by means of a suitable expanding element so as to be adapted to the bone cavity in all directions, particularly with respect to the curvatures of the bone cavity. The expansion or widening of the flaps also compresses any spongy material which has been used for back-filling of the reinforcement.

Conveniently, the peg may be of a construction so as to define a bone cement barrier.

The flaps of the reinforcement are disposed in circumferential overlapping relation so that direct contact between the cement and the bone tissue are obviated even though the reinforcement may expand. Advantageously, in order to provide a stable cement bed inside the reinforcement, the expansion of the flaps is continued to an extent such that, in the case of a femoral head prosthesis, the thickness of the cement bed between the stem and the mesh is at least two millimeters.

These and other objects and advantages of the invention will become more apparent from the following detailed description taken in conjunction with the accompanying drawings wherein.

Figure 1:
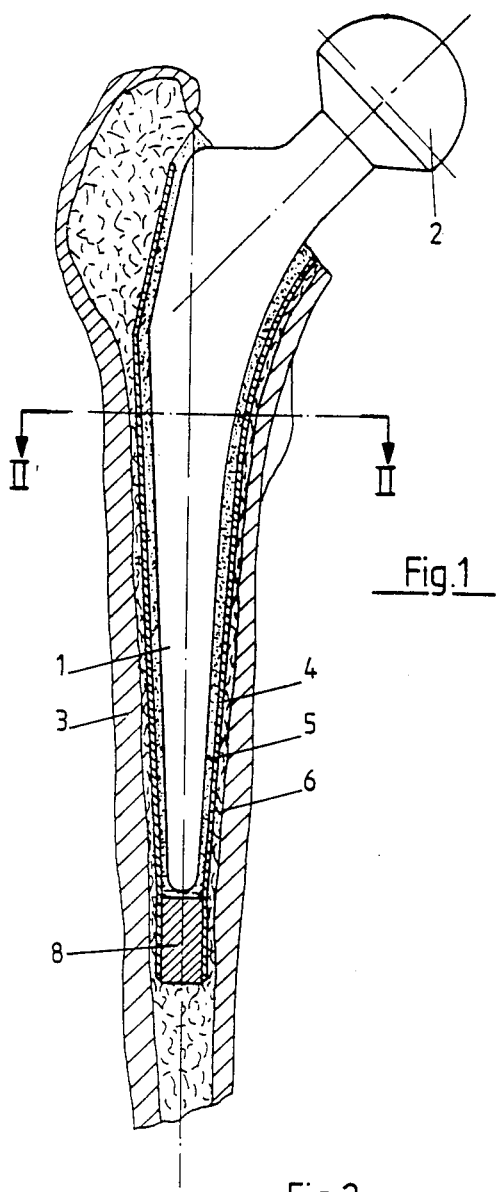
FIG. 1 illustrates a diagram view in longitudinal section of a femoral head prosthesis anchored in a femur by means of a reinforcement in accordance with the invention.
Figure 2:
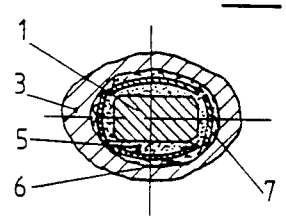
FIG. 2 illustrates a view taken on line II—II of FIG. 1.

Referring to FIGS. 1 and 2, a straight stem 1 of a femoral head prosthesis 2 is fixed or anchored in a femur bone 3 with the interposition of a mesh reinforcement 4 which separates a bone cement bed 5 therein from a layer 6 of spongy bone tissue within the bone 3. The layer 6 is formed by spongiosa which may have been previously obtained during an operation from the operation cavity and used, after possible crumbling, to backfill the reinforcement 4 externally. In this case, the spongiosa is also compressed.

Figure 3:
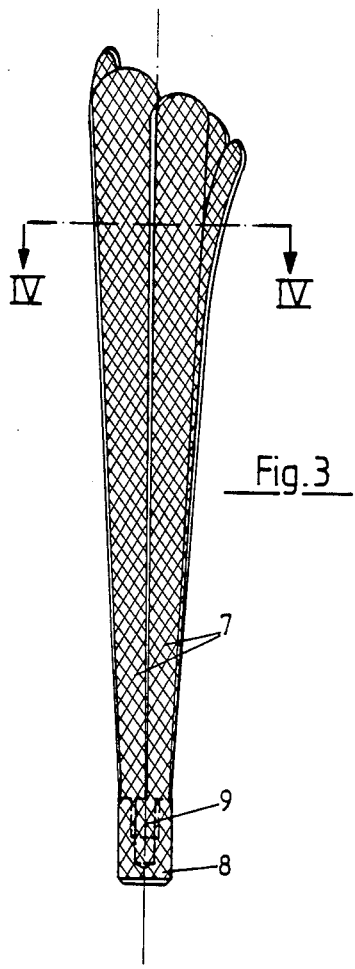
FIG. 3 illustrates a side view of a modified reinforcement in accordance with the invention.

Referring to FIG. 3, the reinforcement 4 is formed of a plurality of discrete flaps 7 which are secured at the distal ends on a peg or pin 8, for example, by welding, if necessary in an overlapping manner. The flaps 7 are made of a porous construction, for example, consisting of one or more layers of a metal wire mesh or lattice made of titanium alloy. In addition, the flaps 7 are radially spaced apart to define tangentially directed slots (FIG. 4) which extend over the entire height of the flaps 4.

Figure 4:
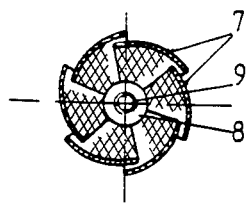
FIG. 4 illustrates a view taken on line IV—IV of FIG. 3.

As illustrated in FIG. 1, the flaps 7 of the reinforcement 4 are of a length to surround a major portion of the stem 1 of the prosthesis 2 in a sleeve-like manner. In addition, as indicated in FIG. 4, the flaps 7 are disposed in circumferential overlapping relation.

The peg 8 is made of a solid construction and is operative, in known manner, as a bone cement barrier. The peg 8 may also have a tapped bore 9 (see FIGS. 3 and 4) to secure a setting instrument (not shown) therein.

In order to substantially preclude direct contact between the bone cement bed 5 and the compacted tissue in the layer 6 despite spreading of the flaps 7, the flaps 7 may overlap one another in the peripheral direction, for example, in calyx-fashion both in the "normal" state (FIG. 4) and the expanded state.

Conveniently, in order to provide a strong cement bed 5, the dimensions of the reinforcement 4 and the stem 1 are so adapted to one another that the cement bed 5 is at least two millimeters thick.

During a surgical procedure, the femur bone 3 is first prepared to form a bone cavity. Thereafter, the cavity is back-filled with the spongiosa and the reinforcement 4 is inserted in place with the peg 8 being inserted via a suitable setting instrument (not shown).

At this time, the flaps 7 may be expanded by a suitable expanding element so as to adapt to the curvatures within the cavity, for example as indicated in FIG. 2. During this time, each flap 7 is free to deform locally to adapt to the contour of the bone cavity under the forces applied by the expanding element. Thereafter, bone cement is placed within the reinforcement and the stem 1 of the prosthesis 2 inserted.

The invention provides a reinforcement which can be put in place and expanded so as to adapt to the contours of a bone cavity in all directions.

The invention also provides a reinforcement which can be radially adapted to the anchoring stems of prosthesis of different cross-sectional sizes and shapes.

What is claimed is:

1. A mesh reinforcement for anchoring an endoprosthesis stem comprising:
    a peg for mounting in an operatively prepared bone cavity; and a plurality of discrete elongated flaps secured to and extending from said peg in circumferential overlapping relation to define a cavity to receive a bone cement for implantation of an endoprosthesis stem therein, said flaps being of a length to surround a major portion of the stem in a sleeve-like manner and being made of porous construction and being spaced apart to define slots therebetween extending over the length of said flaps to permit circumferential expansion of said flaps.

2. A mesh reinforcement as set forth in claim 1 wherein said peg is of solid construction to define a bone cement barrier.

3. A mesh reinforcement as set forth in claim 1 wherein each flap is deformable to permit adaptation to a bone cavity.

4. In combination,
an endoprosthesis having a stem for mounting in a medullated bone; and
a reinforcement having a peg and a plurality of discrete porous mesh elongated flaps secured to and extending from said peg in circumferential overlapping relation to define a cavity to receive a bone cement for implantation of said stem therein, said flaps being of a length to surround a major portion of said stem in a sleeve-like manner and being disposed in spaced relation about said stem to define a plurality of circumferentially spaced slots therebetween extending over the length of said flaps.

5. The combination as set forth in claim 4 wherein said flaps are spaced from said stem a distance of two millimeters.

* * * * *